United States Patent
Todor et al.

(10) Patent No.: US 9,474,493 B2
(45) Date of Patent: Oct. 25, 2016

(54) 3D TRACKING OF AN HDR SOURCE USING A FLAT PANEL DETECTOR

(75) Inventors: Dorin A. Todor, Richmond, VA (US); Aditya A. Bondal, Madison, WI (US)

(73) Assignee: Virginia Commonwealth University, Richmond, VA (US)

( * ) Notice: Subject to any disclaimer, the term of this patent is extended or adjusted under 35 U.S.C. 154(b) by 767 days.

(21) Appl. No.: 13/459,057

(22) Filed: Apr. 27, 2012

(65) Prior Publication Data

US 2012/0277570 A1 Nov. 1, 2012

Related U.S. Application Data

(60) Provisional application No. 61/479,434, filed on Apr. 27, 2011.

(51) Int. Cl.
| | |
|---|---|
| A61B 5/05 | (2006.01) |
| A61B 6/12 | (2006.01) |
| A61N 5/10 | (2006.01) |
| G06T 7/20 | (2006.01) |
| A61B 6/00 | (2006.01) |

(52) U.S. Cl.
CPC .............. *A61B 6/12* (2013.01); *A61B 6/5211* (2013.01); *A61N 5/1007* (2013.01); *G06T 7/2033* (2013.01); *A61B 6/4233* (2013.01); *A61B 6/582* (2013.01); *A61N 2005/1052* (2013.01); *G06T 2207/20148* (2013.01); *G06T 2207/30004* (2013.01); *G06T 2207/30204* (2013.01); *G06T 2207/30241* (2013.01)

(58) Field of Classification Search
CPC .......... A61B 2019/5458; A61B 19/00; A61N 5/1049; A61N 5/1065
USPC ......... 600/407, 410, 426–427; 378/164, 205, 378/20, 62
See application file for complete search history.

(56) References Cited

U.S. PATENT DOCUMENTS

| | | | |
|---|---|---|---|
| 6,405,072 B1 * | 6/2002 | Cosman | 600/426 |
| 6,484,049 B1 | 11/2002 | Seeley et al. | |
| 6,490,475 B1 * | 12/2002 | Seeley et al. | 600/426 |
| 2002/0131559 A1 | 9/2002 | Launay et al. | |
| 2003/0194057 A1 * | 10/2003 | Dewaele | 378/210 |

(Continued)

FOREIGN PATENT DOCUMENTS

WO 03020114 A2 3/2003

OTHER PUBLICATIONS

Keall et al (The management of respiratory motion in radiation oncology report of AAPM Task Group 76).*

(Continued)

*Primary Examiner* — Joel F Brutus
(74) *Attorney, Agent, or Firm* — Whitham, Curtis & Cook, P.C.

(57) ABSTRACT

A method and apparatus are used to compare in real-time an intended radiation treatment plan with a delivered plan. Markers are arranged, on a subject receiving radiation, at three-dimensional (3D) positions between a two dimensional radiation detector and a radiation source and are used to reconstruct the actual position of a high dose rate (HDR) source in three-dimensional (3D) space. The detected position is compared with the intended radiation path of the treatment plan. Adjustments can be made to the treatment plan if the detected position and the intended path do not correspond.

17 Claims, 10 Drawing Sheets

(56) References Cited

U.S. PATENT DOCUMENTS

| | | | |
|---|---|---|---|
| 2004/0158146 A1* | 8/2004 | Mate et al. ................... 600/427 |
| 2005/0117708 A1* | 6/2005 | Cho et al. .................... 378/164 |
| 2006/0027756 A1* | 2/2006 | Thomson et al. ....... 250/370.07 |
| 2008/0002811 A1 | 1/2008 | Allison |
| 2008/0275341 A1 | 11/2008 | Fehre et al. |
| 2009/0154646 A1* | 6/2009 | Carol et al. ..................... 378/65 |
| 2010/0312038 A1* | 12/2010 | Shechter ............. A61N 5/1015 600/3 |

OTHER PUBLICATIONS

Bondal, "Real-Time 3-D Tracking of the High Dose Rate Radiation Source Using a Flat Panel Detector", VCU Theses and Dissertations, Aug. 30, 2010, p. 5-6;26-28;46;68-69;73.

Lindsey, "The Derivation and Testing of Three-Dimensional Line Equations that Predict the Location of Brachytherapy Sources", Wright State University Thesis, Sep. 2, 2010, p. 1-11;72-73.

Song et al., "Tracking Brachytherapy Sources Using Emission Imaging with One Flat Panel Detector", Medical Physics AIP, Mar. 10, 2009, p. 1109-1111.

\* cited by examiner

3D TRACKING OF AN HDR SOURCE USING A FLAT PANEL DETECTOR

CROSS REFERENCE TO RELATED APPLICATION

The invention disclosed in the present application is based on the invention disclosed in U.S. Provisional Patent Application Ser. No. 61/479,434 filed Apr. 27, 2011. Benefit of the filing date of U.S. Provisional Patent Application Ser. No. 61/479,434 of the commonly disclosed invention is claimed.

BACKGROUND OF THE INVENTION

1. Field of the Invention

The present invention generally relates to a method and apparatus for reconstructing the position of a high dose rate (HDR) source in three-dimensional (3D) space in real-time using a flat panel detector (FPD) and can be used to compare the detected position with the path produced by the treatment plan.

2. Background Description

Brachytherapy involves two distinct phases, a planning phase and a treatment phase. The planning phase, which produces a treatment plan, typically involves subjecting the patient to CT scan, an MRI or ultrasound imaging in order to determine the 3D coordinates of the locations within the patient's body where radiation therapy is to be applied. The treatment phase requires placing the radiation emitting or HDR source at those locations determined in the planning phase according to the treatment plan.

During HDR treatments, the source follows a path through catheters and applicators based on a plan produced by the treatment planning phase. A number of Quality Assurance (QA) procedures are put in place to safely deliver a treatment as planned. Evaluating whether the treatment is or has been delivered as planned is difficult because a typical treatment plan is a list of source positions and time intervals. The source position may be defined as distances from/the end of the catheter along the catheter (i.e., along a trajectory). In order to compare the applied treatment with the planned treatment, the planned source positions and the reconstructed source positions have to be expressed in the same coordinate system. Thus, a correspondence between a detection coordinate system and a planned coordinate system has to be established. As known in the art, such a conversion is generally an overlap of a 3D translation and a 3D rotation with a scale factor, if necessary. The problem of establishing a correspondence between a detection coordinate system and a plan coordinate system is even more complex due to the manner in which the plan sets forth the source positions (i.e., distances on a trajectory from an end thereof). Conventionally, it was assumed that the plan was delivered as intended, but no feedback was generated. That is, no comparison of applied treatment with the planned treatment was performed. Moreover, this must be done in real time, to determine that the real HDR positions and the dwell times correspond to the treatment plan. This might be done using, for example, a fluroscope image of the catheter. However, this procedure subjects the patient to a double dose of radiation if the planning phase was conducted using a CT scan, for example. The Nuclear Regulatory Commission (NRC) prohibits using two sources of radiation simultaneously (for instance an X-ray source for imaging and an HDR source for treatment delivery).

SUMMARY OF THE INVENTION

It is an object to provide methods, apparatuses and a computer readable medium configured and capable to enable a comparison between an intended treatment plan and an actually delivered treatment, by reconstructing the radiation source position based on projections of markers at known locations on an image acquired using a two-dimensional radiation detector. One or more of the independent claims advantageously provides the possibility to make a real-time comparison between the intended treatment plan and the actually delivered treatment automatically, free of human error.

According to an exemplary embodiment, there is a method for comparing an intended treatment plan with a delivered plain. The method includes arranging markers (e.g. at least two markers) at three-dimensional (3D) positions (typically known positions, which are arranged according to the delivery plan) in a detection reference system. The markers are located between a radiation detector (e.g. a two dimensional radiation detector) configured to acquire images generated by radiation emitted by a radiation source (e.g. at least one radiation source) and an area where the radiation source is positioned during a treatment. The method further includes determining positions of (e.g. detecting) projections of the markers on an image detected when the radiation source is at a treatment position in an intended treatment plan reference system. The method further includes calculating a plurality of lines, each line being defined by a 3D position of a marker and a 3D position of a corresponding projection of the marker on the detector according to the image, in a detection reference system. The method further includes inferring a 3D position of the radiation source in the detection reference system, based on the calculated lines. Further, if no correspondence between the detection reference system and the intended treatment plan reference system is available, the inferred 3D position is matched with the treatment position to extract the correspondence between the detection reference system and the intended treatment plan reference system. If the correspondence between the detection reference system and the intended treatment plan reference system is available, the inferred 3D position is compared with the treatment position.

According to another exemplary embodiment, there is a computer readable medium transitory storing executable codes which when executed on a computer make the computer perform a method for comparing an intended treatment plan with a delivered plan. The method includes arranging markers at known three-dimensional (3D) positions in a detection reference system, the markers being located between a two dimensional radiation detector configured to acquire images generated by radiation emitted by a radiation source and an area where the radiation source is positioned during a treatment. The method further includes determining positions of projections of the markers on an image detected when the radiation source is at a treatment position in an intended treatment plan reference system. The method further includes calculating a plurality of lines, each line being defined by a 3D position of a marker and a 3D position of a corresponding projection of the marker on the detector according to the image, in a detection reference system. The method further includes inferring a 3D position of the radiation source in the detection reference system, based on the calculated lines. Further, if no correspondence between the detection reference system and the intended treatment plan reference system is available, the inferred 3D position is matched with the treatment position to extract the correspondence between the detection reference system and the intended treatment plan reference system. If the correspondence between the detection reference system and the intended treatment plan reference system is available, the inferred 3D position is compared with the treatment position.

According to another exemplary embodiment, there is an apparatus for comparing an intended treatment plan using a radiation source with a delivered plan. The apparatus includes a two-dimensional radiation detector, a plurality of markers and a data processing unit. The apparatus is configured to acquire images generated by radiation emitted by the radiation source at a planned 3D position of the radiation source according to the intended treatment plan. The markers are arranged at known three-dimensional (3D) marker positions, between the detector and the planned 3D position of the radiation source according to the intended treatment plan. The data processing unit is configured: (1) to determine projections of the markers on an image detected when the radiation source is located at a treatment position; (2) to calculate a plurality of lines, each line being defined by a 3D position of a marker and a 3D position of a corresponding projection of the marker on the detector according to the image; (3) to infer a 3D position of the radiation source based on the calculated lines; and (4) to compare the inferred 3D position with the planned 3D position.

According to another embodiment, there is a method for real-time method for three dimensional (3D) high dose rate (HDR) source position detection and tracking and for comparing, in real-time, an intended treatment plan with a delivered plan. The method according to this embodiment begins with developing the intended treatment plan by scanning a patient in a first 3D coordinate system. A flat panel detector (FPD) having a matrix of markers with precisely known locations on the FPD at variable heights is placed over the patient. Projections of markers as images on the FPD produced by the HDR source at multiple dwell positions are detected. Images of the markers are processed to obtain a calculated relative position of the HDR source in a second 3D coordinate system at each of the multiple dwell positions. Then, a transformation calculation is performed of coordinates from the second 3D coordinate system to the first 3D coordinate system. Detected positions of the HDR source at each of the multiple dwell positions is compared with corresponding-intended dwell positions according to the intended treatment plan. The process is performed in real-time to provide a direct correlation of delivered treatment plan with the intended treatment plan.

The treatment position of the radiation source may be inside or on a patient's body. The radiation source may be a high dose radiation (HDR) source having an activity, of few Curies (e.g., 3 Ci). The time for acquiring a useable image is inversely proportional with the activity of the source, e.g., the larger the activity of the source the shorter the time necessary to acquire the image.

The projections of the markers are fuzzy mostly due to radiation scatter between the source and the detector. The positions of the projections are extracted from the image, for example, using morphological segmentation. Here it should be understood that the image is not a sharp image and thus identifying the shapes of the projections and enhancing the image by filtering noise are necessary to determine the positions of the projections.

In order to infer the 3D position of the source, for each pair of lines it is determined an estimated position of the source. If the lines of a pair intersect, the estimated position of the source is the point of intersection; but if the lines do not intersect, a distance of closest approach is determined and the coordinates of the inferred position are the middle point of this distance. The inferred 3D position may be median or average of the estimated positions. Prior to determining the inferred 3D position, outlier estimated positions may be eliminated or weighted such as to lower their importance in the average.

The above-described embodiment of inferring the 3D position is exemplary and it is not intended to be limiting. One can foresee grouping three lines and finding a distance from the detector at which an area of a triangle defined by intersections of each of the lines with a plane parallel to the detector is smallest; the estimated position of the source then may be considered the center of this triangle coupled with the distance.

The intended treatment plan is defined as sets of positions along a trajectory and exposure times. Initially the correspondence between the detection reference system (two-dimensional (2D) detector and a distance from the detector) and this intended treatment plan reference system is available. It is assumed that the first inferred 3D position corresponds to the first position in the intended treatment plan, the second inferred 3D position corresponds to the second position in the intended treatment plan, and so forth. The inferred positions are determined with a limited precision. Upon combining (matching) enough of the inferred 3D position with corresponding positions in the intended treatment plan, a satisfactory conversion of the position in the intended treatment plan into the detection reference system may be achieved. Then following positions in the intended treatment plan can be converted into the detection reference system and compared directly with the inferred 3D positions.

During tests, the markers were arranged in a square grid on the cover of the detector in a plane. However, this geometry was convenient but it is not intended to be limiting. For example, arranging the markers on a sphere or parabolic surface may have focusing effects enhancing the resolution of inferring the 3D position. Another regular or irregular pattern of the markers may be employed and more effective for different the treatment plans. Here it is emphasized evaluating quality of the treatment, that is, the deviation of the position of the source from the planned position should not exceed what is considered acceptable. Not all coordinates have the same importance; the x-y position is more important than the z position, which is more affected by the patient's breathing.

The acceptable position deviations cannot be less than the uncertainties, but they may be more. The acceptable position deviations may be the larger of the uncertainties and predetermined values.

The invention provides the potential to correct the applied treatment when it departs too much from the intended treatment. More specifically, an alarm may be a message or any visual or otherwise indication urging the operator's attention. One may imagine protocols (software implemented) in which the alarm would be triggered by repeated and successive instances of the one or more differences exceeding acceptable position deviations.

Prior to starting, the treatment, without the patient body between the source and the detector and with the source at a known fixed position, the known three-dimensional (3D) positions may be confirmed and an origin of a reference coordinate system may be established by acquiring and analyzing a sharp image. The perpendicular wires may define an origin of the horizontal coordinates and may correspond to the known fixed position of the source.

The quality rules may be related to quality of the projection of the marker on the detector. If the projection is fuzzier, there is more uncertainty to associating coordinates to the image. Further down in inferring the source position the quality rules may be related to impact of a line if inferring the 3D position. For example, if a distance from one line to all the other lines is larger than a predetermined threshold, this one line should be removed from the subset-used to infer the 3D position.

Identifying the marker projections on the image means associating a projection to a marker. The projections are fuzzy and there may be a lot of background noise. Some projections may overlap or otherwise become un-useable, being "eliminated" from the further processing; i.e., an embodiment of projection quality rules. The position estimation rules may be to use center of the marker projections or "lightest spot" of the projection.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE INVENTION

The following description of the exemplary embodiments refers to the accompanying drawings. The following embodiments are discussed, for simplicity, with regard to the terminology and structure of a brachytherapy treatment methodology. Reference throughout the specification to "one embodiment" or "an embodiment" means that a particular feature, structure, or characteristic described in connection with an embodiment is included in at least one embodiment of the present invention. Thus, the appearance of the phrases "in one embodiment" or "in an embodiment" in various places throughout the specification is not necessarily all referring to the same embodiment. Further, the particular features, structures or characteristics may be combined in any suitable manner in one or more embodiments.

In the conventional X-ray, the patient's body is the unknown and the source is known. In the present invention, the source position is unknown and the markers' positions and sizes are known. The radiation from the HDR source is detected by a flat panel detector (FPD). A matrix of markers (in the form of 4 mm ball bearings) with precisely known locations is placed between the source and the FPD at variable heights. Using segmentation and noise reduction algorithms, the location of the radiation source can be determined with sub-millimeter precision based on the image of the markers on the FPD.

Segmentation and noise reduction algorithms are applied to the image. The segmentation algorithm automatically segments and labels the markers' images. In addition, a mathematical solution for "near-intersection" of two 3D lines was implemented and used to determine the "true" 3D source position. Software is used to match or compare the reconstructed source position with the actual treatment plan. A radiation therapy procedure is typically delivered after lumpectomy as part of the breast conservation solution. There might be as many as 20-30 catheters with as many as 200-300 positions with short dwell times. Correspondence between the planning coordinate system and the treatment coordinate system, can be determined after the detection of between four and ten positions of the HDR source.

Figure 1:
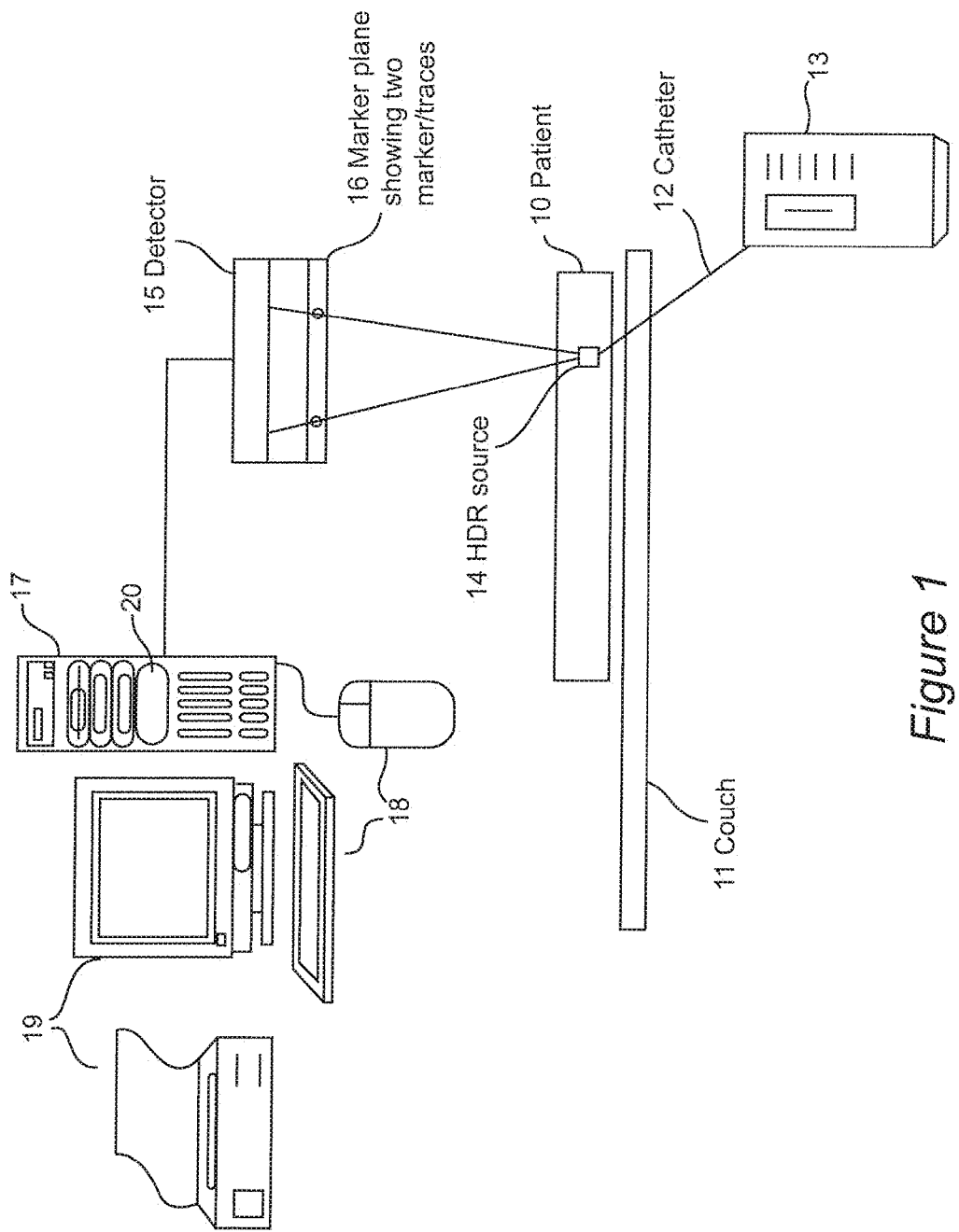
FIG. 1 is a block diagram illustrating the arrangement of the system using a flat panel detector to track an HDR source in a patient.

Referring now to the drawings, FIG. 1 illustrates a block diagram of the system using a flat panel detector to track a radioactive source in a patient as explained above. More specifically, a patient 10 is lying on a treatment couch 11. A catheter 12 is connected to an afterloader 13. Although a single catheter is represented in the drawing figure, there might be as many as 20 catheters with as many as 200-300 dwell positions within the patient 10. The radioactive source 14, which may be a high dose radioactive (HDR) source, is positioned accurately in a remote afterloader 13 and travels through the catheter into or on the patient. Positioned above the patient in this illustration is a flat panel detector (FPD) 15, and superposed between the FPD 15 and the patient 10 is a marker panel 16, described in more detail with reference to FIG. 2. The location illustrated in FIG. 1 is exemplary and not intended to be limiting. The FPD 15 can be located anywhere else relative to the patient 10 such that to minimize the attenuation and scattering of me radiation traveling from the HDR source 14 to the FPD 15.

The output of the FPD 15 is supplied to a computer 17 having a user interface (UI) 18 and output 19. The UI 18 may take the form of a keyboard, a pointing device, such as a mouse or trackball, and media reader, either magnetic or optical. The output 19 may take the form of a display, printer and media writer. The computer 17 is typically a desk top computer having a multi-core processor and sufficient random access memory (RAM) and magnetic disk storage to perform the image-processing and real time calculations required to perform the processes described. Software implementing the invention may be stored onto non-transitory computer readable media, such a magnetic or optical storage media, and loaded onto the memory 20 of the computer 17.

Figure 2:
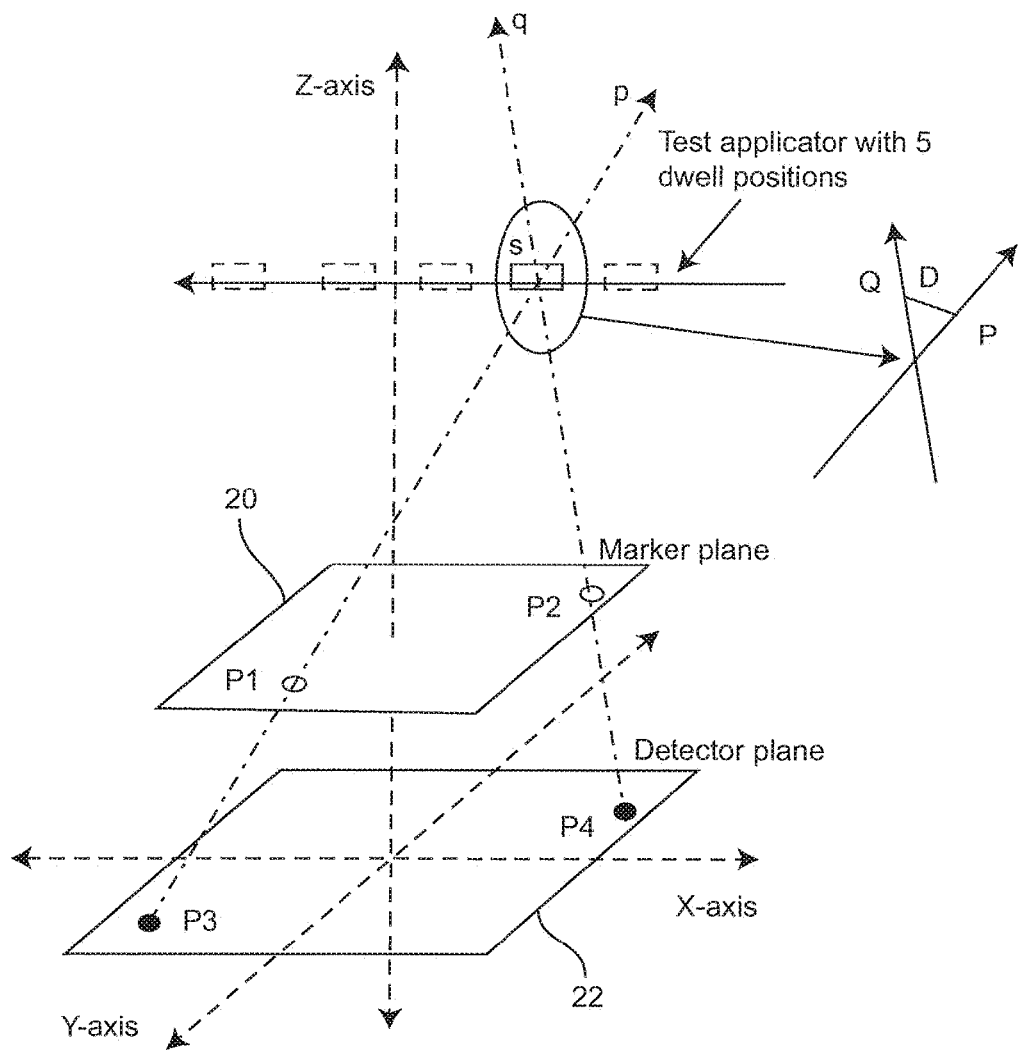
FIG. 2 is a schematic representation of the construction of the flat panel detector (FPD) according to one aspect of the invention.

Referring now to FIG. 2, there is shown schematic representation of the flat panel detector (FPD) 15 in combination with the marker panel 16 according to an embodiment of the invention. The FPD 15 and marker panel 16 form two planes, a detector plane panel 20 and a parallel marker plane panel 22. The marker plane panel 22 may be made of plastic and machined to provide a precision matrix of holes to receive markers spaced 2 cm apart, with the center of the matrix coinciding with the center of the EPID. In this exemplary embodiment, ball bearings of 4 mm in diameter are used as markers. The matrix of markers makes up the marker plane 22 ($P_1$ and $P_2$), while the projection of these markers makes up the detector plane 20 ($P_3$ and $P_4$). Images acquired using an x-ray source are used to calibrate the system, to get the height between the detector plane 20 and the marker plane 22 and to get the coordinates of the markers ($P_1$ and $P_2$) in 3D space with reference to the center of the detector as the origin of the coordinate system, while the HDR source is used for treatment. The marker positions are always fixed. For every position of the HDR source, each marker will have a unique projection. The point of intersection of two lines defined by a marker and its projection gives the position of the HDR source. Markers produce projections on the detector plane 10. Coordinates of the markers and of the projections are calculated. Lines are defined in 3D space for each marker-projection pair.

Tracking of the HDR source at point S at one of a plurality of dwell positions according to the treatment phase is illustrated in FIG. 2. $P_1$ and $P_2$ represent two markers placed at known positions on the marker plane 22. The system of axes is chosen such that the center of the detector acts as the origin, the x-axis and the y-axis run through the center of the detector and the z-axis is perpendicular to the plane of the detector. For purposes of explanation, it is assumed that point S is one of the dwell positions where the HDR source will be active for a certain amount of time, i.e., the dwell time. When the HDR source reaches point S and is active, it will produce projections of the markers on the detector. Thus, marker $P_1$ will produce projection $P_3$ on the detector plane 20 while marker $P_2$ will produce projection $P_4$ on the detector plane 20. Once the coordinates of the markers and their projections with respect to the origin are known in 3D space, a line which passes through the marker and its projection can be defined. Line p is defined by the combination of marker $P_1$ and its projection $P_3$ while line q is defined by the combination of marker $P_2$ and its projection $P_4$. The intersection of these two imaginary lines p and q in 3D space will give the position of the HDR source at point S. The same procedure is repeated to track all other dwell positions of the HDR source.

Figure 3:
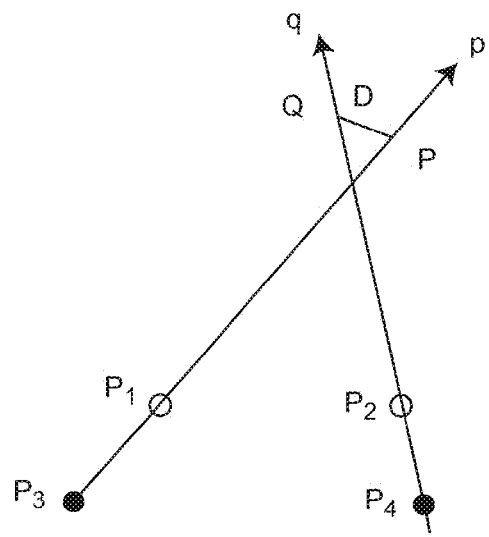
FIG. 3 is a schematic illustration of two non-intersecting projection lines showing the determination of the shortest distance D between the lines.

It is not necessary for two non-parallel lines to intersect in space. Most non-parallel lines do not have any points in common. They go over and under one another without touching. Thus, to plot the true intersection of the line p and the line q in space is very unlikely. Instead, the shortest distance between the two lines is computed as an alternative to a "real" intersection. When two lines in 3D space do hot intersect, they can be connected by a line segment. The shortest such line segment is unique and is considered to be the "true" intersection of the two lines in 3D space. The shortest distance between line p and the line q is represented by D, as illustrated in FIG. 3 where P and Q represent the corresponding two points contained on the lines p and q, respectively, that define the line D. The mean of the coordinates of points P and Q gives an estimate of the 3D coordinates of the source position best for this situation.

While the schematic representation of FIG. 2 represents only two markers, it will be understood that a well defined matrix of markers is used. A single, pair of markers and their projections yield an estimation of the source position. The above procedure is repeated for all possible combinations of marker/projection pairs. N markers would produce $N*(N-1)/2$ combinations of marker/projection pairs, each pair producing an estimate position. The average over all estimated positions gives the most accurate position reconstruction of the source at any point in time.

Figure 4:
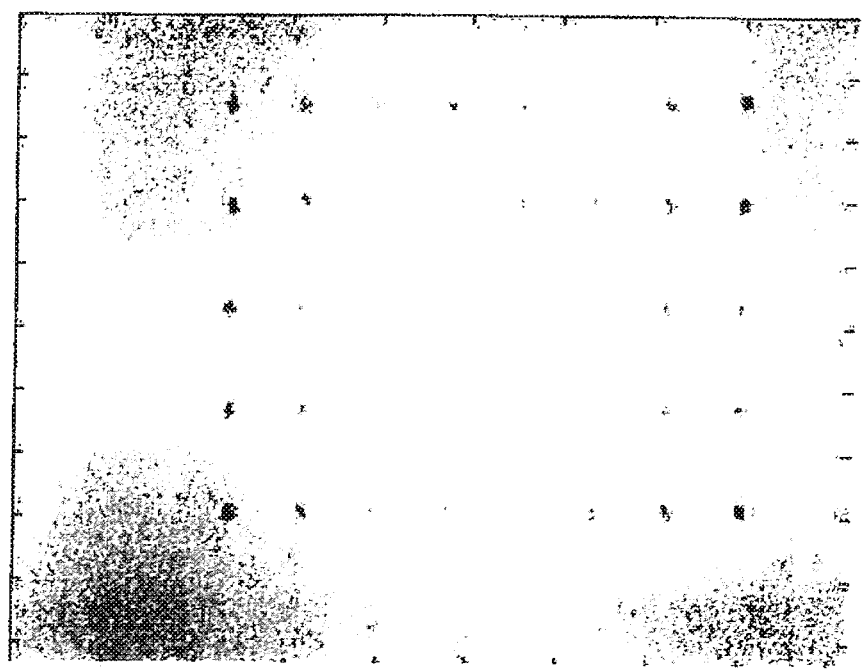
FIG. 4 is a grey scale image, averaged and cropped, acquired using an HDR source and the flat panel detector (FPD)

An image data set is acquired and stored by the computer 17, shown in FIG. 1. In an exemplary embodiment, at least one image, and generally multiple images for each dwell position are acquired and stored. Image averaging is performed and a blank image (containing only noise) is subtracted for noise reduction. The idea of averaging is Signal to Noise Ratio (SNR) improvement. Without being bound by theory, it is believed that if a weak signal is acquired in the presence of noise, the signal is coherent but the noise is not. Thus, when multiple measurements are added together, multiple coherent signals will "stack up" while the noise will cancel out, resulting in a detectable signal unencumbered by noise. In other words, the concept of image averaging is that when the five images are added together, the random fluctuations of the noise above and below the projections of the markers will gradually cancel each other out, thus increasing the signal to noise ratio (S/N) of the image by removing major components of noise. Those of skill in the art will recognize that the number of images acquired is a compromise between the desire to increase the SNR and the time needed to acquire multiple images. While one would choose a very large number of images to be averaged in order to improve marker projection detection, one also has to minimize the total acquisition time, taking into account the relevant time resolution of the process that is being monitored. Averaging over, for example, from at least about two to about 10, or from about 5 to about 10 (or more), images helps to reduce the noise in the image. The projection of the markers holds a value (pixel intensity) that depends on the location and strength of the source, but which is fixed across the multiple images that are acquired. Noise is assumed to be truly random. Even after image averaging, unwanted noise may be observed along the borders of the image. This noise is removed by simply cropping twenty five pixels off each border of the image. FIG. 4 is a grey scale image after being averaged and cropped for one of the dwell positions.

Morphological image processing of the marker image data involves isolating and segmenting the markers, sorting the projections of the makers in accordance with the relative position of the markers obtained from the calibration image. The shape and size of the markers that have to be isolated from the image are known before hand. For this reason, morphological image processing is performed to isolate the projection of the markers and obtain the coordinates of the centroid. The "imbothat" command from the Matlab image processing toolbox is used to perform morphological bottom-hat filtering on the grey scale image. The MorphologicalBottomHat object performs bottom-hat filtering on an intensity or binary image. Bottom-hat filtering is the equivalent of subtracting the input image from the result of performing a morphological closing operation on the input image. The bottom-hat filtering object uses flat structuring elements only.

A bottom-hat filter enhances black or dark spots in a white background. It subtracts the morphological closing of the image from the image (see below for a description of closing).

Closing: Performs a dilation followed by an erosion. The effect is to fill holes and join nearby objects.

Erosion: For binary, replaces any 1 pixel by 0 if any of its neighbors is 0. For grayscale, each pixel is replaced by the minimum of its neighbors and itself.

Dilation: For binary, replaces any 0 pixel by 1 if any of its neighbors is 1. For grayscale, each pixel is replaced by the maximum of its neighbors and itself.

The bottom-hat filter requires a structuring element which would define the shape of the markers. The markers are substantially circular structures, so the first step is to define a structuring element of the type "disk" This is done by using the "strel" function. The filtered image is then stored. An example of the "imbothat" and "strel" functions is explained as follows:

se=strel('disk',25);

I1=imbothat(I,se);

The above code creates a flat, disk-shaped structuring element "se" with a radius of 25 pixels. The bottom-hat function is performed on the cropped image I using "se" and stores it in I1. Other than the bottom-hat filter, two more filters are used in order to reduce noise. First, a wiener2 filter is used. Wiener2 is a 2D pixel-wise adaptive Wiener filtering method which acts as a lowpass filter to improve a degraded grey scale image by removing noise. It is based on statistics estimated from a local neighborhood of each pixel. Next, a medfit2 filter is used. Medfit2 is a 2D nonlinear median filtering method which is used to reduce "salt and pepper" noise. The code for the two filters is as follows:

[I2,noise]=wiener2(I1,[15 15]);

I3=medfilt2(I2,[8]);

A 15×15 pixel size neighborhood is used to estimate the local image mean and standard deviation to perform the wiener2 filtration method on the image I1 and the filtered image is stored in I2. A 8×8 pixel size neighborhood is used around each pixel in I2 to perform the median filtration method and the filtered images are stored in I3.

Next, the markers are isolated. The grey scale image is converted into a binary image such that only the markers take the value 1 while the rest of the image is 0. This is done by applying a threshold to the image.

I4=I3>means2(I2)+2.5*std2(I3);

The mean value plus 2.5 times the standard deviation value is used as the threshold applied to image I3 and the binary image is stored in I4. From the binary image I4 the markers can be isolated, labeled and the centroid for each marker can be calculated using the following code:

[I5,NUM]=bwlabeln(I4);

STATS=regionprops(I5,'Centroid','Area');

The "bwlabeln" function labels the markers in image I4 and saves it in I5. The "regionprops" function measures the centroid and area of the labeled markers in image I5 and stores it in the array STATS. The x-y pixel coordinates of the centroids can be accessed using the Comma-Separated List Syntax explained as follows:

STATS.Centroid

The Centroid acts as a substitute for the coordinates of the markers and is represented by the pixel number. In order to obtain the coordinates with respect to the system of chosen axes, the x and y coordinates of the pixel number of the centroids have to be subtracted by the center of the detector. The coordinates are converted into centimeters by multiplying the pixel number with the pixel size or the resolution of the flat panel detector.

When the labeling of the segmented image is performed, the markers get labeled in any random order. Thus, the labeled markers need to be rearranged such that the same order for the markers on the calibration image and the projection of the markers on the image acquired by the HDR source have the same order. This is done by using the "sort" command in Matlab. The sorted coordinates of the projections are stored in a variable called "img" while the sorted coordinates of the markers are stored in a variable called "cal". The following is the code used to sort the marker image.

```
N = length(STATS);
for i = 1:n
    areas(i) = STATS(i).Area;
    xx(i) = STATS(i).Centroid(1);
    yy(i) = STATS(i).Centroid(2);
    xx1(i) = 0.0388*(xx(i)-487);
    yy1(i) = 0.0388*(359-yy(i));.
end;
[cent_y,IM_y] = sort(yy);n-1;img=[ ];
for i= 1:5
    IMG1 = IM_y(n:n+7);
    IMG2 = sort(IMG1);
    img = [img IMG2]
    n = n+8;
end
``` where 0.0388 is the resolution of the detector, (487,359) is the center of the cropped image.

Figure 5:
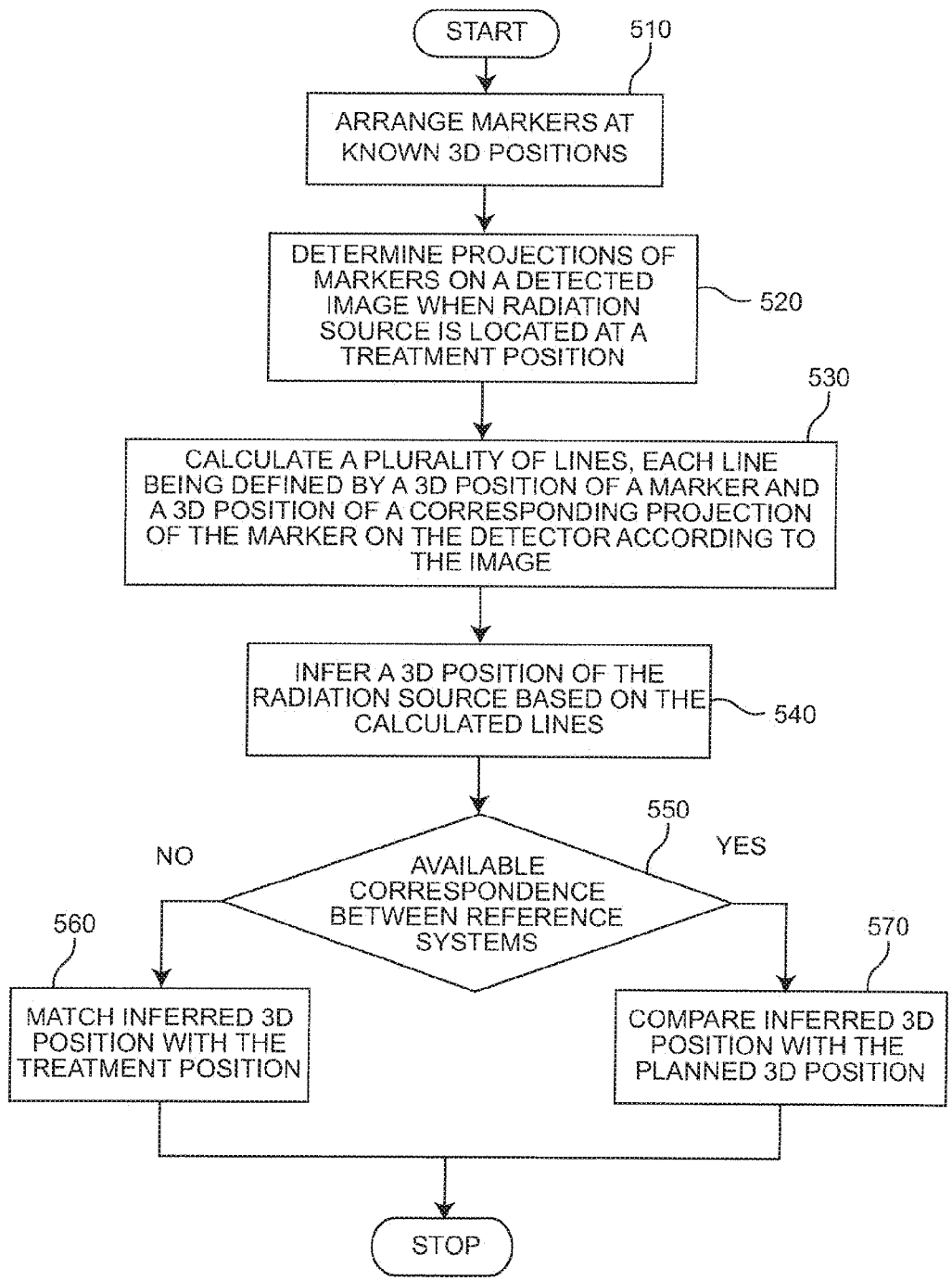
FIG. 5 is a flow diagram summarizing the method according to the invention.

FIG. 5 is a flow diagram summarizing a method according to and embodiment of this application. The first step 510 is to arrange markers at known 3D locations. Next, at 520, the projections of markers on a detected image is determined when a radiation source is located at a treatment position. Then at 530, a plurality of lines are calculated, each line being defined by a 3D position of a marker and a 3D position of a corresponding projection of the marker on the detector according to the image. From the calculated lines, a 3D position of the radiation is inferred at 540. A determination is made at 550 as to whether there is available correspondence between reference systems. If no correspondence between the detection reference system and the intended treatment plan reference system is available, the inferred 3D position is matched with the treatment position to extract the correspondence between the detection reference system and the intended treatment plan reference system at 560. If the correspondence between the detection reference system and the an intended treatment plan reference system is available, the inferred 3D position is compared with the treatment position at 570. The intended treatment plan is defined as sets of positions along a trajectory and exposure times. Initially the correspondence between the detection reference system (2D detector and a distance from the detector) and this intended treatment plan reference system is not available. It is assumed that the first inferred 3D position corresponds to the first position in the intended treatment plan, the second inferred 3D position corresponds to the second position in the intended treatment plan, etc. The inferred positions are determined with a limited precision. Upon combining (matching) enough of the inferred 3D position with corresponding positions in the intended treatment plan a satisfactory conversion of the position in the intended treatment plan into the detection reference system may be achieved. Then following positions in the intended treatment plan can be converted into the detection reference system and compared directly with the inferred 3D positions.

The flat panel detector produced by Varian (Varian Flat Panel Detector: PaxScan 4030CB) is an example of useable detector but it is not intended to be limiting. The treatment position of the radiation source may be inside or on a patient's body. The radiation source may be a high dose source having an activity of few Curies (e.g., 3 Ci). The time for acquiring a useable image is inversely proportional with the activity of the source—the larger the activity of the source the shorter the time necessary to acquire the image. Hence, larger activity sources may be advantageous since longer exposure times can create more noise.

The projections on the images are fuzzy mostly due to radiation scatter between the source and the detector. The positions of the projections are extracted from the image, for example, using morphological segmentation. Here it should be understood that the image is not a sharp image and thus identifying the shapes of the projections and enhancing the image by filtering noise are necessary to determine the positions of the projections.

In order to infer the 3D position, for each pair of lines it is determined an estimated position of the source. If the lines of a pair intersect, the estimated position of the source is the point of intersection; if the lines do not intersect, a distance of closest approach is determined and the coordinates of the inferred position are the middle point of this distance. The inferred 3D position may be median or average of the estimated positions. Prior to determining the inferred 3D position, outlier estimated positions may be eliminated or weighted such as to lower their importance in the average.

The above-described embodiment of inferring the 3D position is exemplary and it is not intended to be limiting. One can foresee grouping three lines and finding a distance from the detector at which an area of a triangle defined by intersections of each of the lines with a plane parallel to the detector is smallest; the estimated position of the source then may be considered the center of this triangle coupled with the distance.

The method of in FIG. 5 is described for one position. In fact the determining, the calculating, the matching or comparing are repeated for a predetermined number of points in the treatment plan, or until a predetermined precision of matching the inferred 3D position with the treatment position is achieved. Then the correspondence between the detection reference system and the intended treatment plan reference system becomes available for performing the comparing. The intended treatment plan is defined as sets of positions along a trajectory and exposure times. Initially the correspondence between the detection reference system (2-D detector and a distance from the detector) and this intended treatment plan reference system is available. It is assumed that the first inferred 3D position corresponds to the first position in the intended treatment plan, the second inferred 3D position corresponds to the second position in the intended treatment plan, etc. The inferred source positions are determined with a limited precision. Upon combining (matching) enough of the inferred 3D position with corresponding positions in the intended treatment plan a satisfactory conversion of the position in the intended treatment plan into the detection reference system may be achieved. Then following positions in the intended treatment plan can be converted into the detection reference system and compared directly with the inferred 3D positions.

In the embodiment illustrated in FIG. 1, the known 3D positions of the markers are substantially in a plane which is substantially parallel to the detector. However, neither being in a plane nor being parallel to the detector are necessary, limiting conditions. In some embodiments, the markers may be arranged in a grid having substantially equal distances there-between, but regularity of the arrangement is not a requirement either. During tests the markers were arranged in a square grid on the cover of the detector in a plane. However, this geometry was convenient but it is not intended to be limiting. For example, arranging the markers on a sphere or parabolic surface may have focusing effects enhancing the resolution of inferring the 3D position. Another regular or irregular pattern of the markers may be employed and more effective for different the treatment plans.

The markers may be substantially spherical and are made of a radiation absorbing material. For example, the radiation absorbing material may be (but it is not limited to) stainless steel or lead.

Comparing the inferred 3D position of the source with the treatment position may includes comparing one or more differences between corresponding coordinates of the inferred 3D position and coordinates of the planned 3D position with one or more acceptable position deviations. Here it is emphasized evaluating quality of the treatment—that is the deviation of the position of the source from the planned position should not exceed what is considered acceptable. Not all coordinates have the same importance; the x-y position is more important than the z position, which is more affected for example by the patient's breathing.

The one or more acceptable position deviations may have predetermined values or may be defined relative to the one or more uncertainties. The one or more uncertainties of one or more coordinates of the inferred 3D position may also be estimated. The acceptable position deviations cannot be less than the uncertainties (for example, if the uncertainty in determining accurately 3D positions during the treatment is 0.5 mm, then only a distance greater than 0.5 mm can be considered a 'deviation'), but they may be more. The acceptable position deviations is generally the larger of the uncertainties and predetermined values. In some embodiments, deviations greater than 2 mm are of concern. However, generally, but generally deviations of from about 1-1.5 mm are indicative of the need for an alert, with a stronger warning occurring at 2 mm, and, optionally, an automatic stop of the treatment delivery for distances for deviations of >2.5-3 mm. Those of skill in the art will recognize that such thresholds are dependent on anatomical sites. For example, applicators (e.g. catheters) placed in the breast will likely move due to normal breathing, in which case a threshold of e.g. 5 mm may be appropriate, whereas for catheters placed in or at a more stationary position (e.g. prostate), smaller deviation thresholds may be suitable.

When the one or more differences exceed the one or more acceptable position deviations, an alarm may be generated. Thus, applying this method provides the potential to correct the applied treatment when it departs too much from the intended treatment. The alarm may be a message or any visual or otherwise indication urging the operator's attention. One may imagine protocols (software implemented) in which the alarm would be triggered by repeated and successive instances of the one of more differences exceeding acceptable position deviations.

In some embodiments, a calibration procedure using substantially perpendicular wires arranged on a plane and placed between the radiation source and the detector may be employed. Prior to starting the treatment, without the patient body between the source and the detector and with the source at a known fixed position, the known three-dimensional 3D positions may be confirmed and an origin of a reference coordinate system may be established by acquiring and analyzing a sharp image. The perpendicular wires may define an origin of the horizontal coordinates and may correspond to the known fixed position of the source.

In some embodiments, a subset of lines is selected based on one or more predetermined quality rules. The quality rules may be related to quality of the projection of the marker on the detector. If the projection is fuzzier, there is more uncertainty to associating coordinates to the image. Further down in inferring the source position the quality rules may be related to impact of a line if inferring the 3D position. For example, if a distance from one line to all the other lines is larger than a predetermined threshold, this one line should be removed from the subset used to infer the 3D position.

The step 530 in FIG. 5 may includes identifying marker projections on die image, estimating 3D positions of the marker projections based on position estimation rules, selecting a subset of projections among the marker projections on the image based on projection quality rules. Identifying the marker projections on the image means associating a projection to a marker. The projections are fuzzy and there may be a lot of background noise. Some projections may overlap or otherwise become un-useable, being "eliminated" from the further processing—i.e., an embodiment of projection quality rules. The position estimation rules may be to use center of the marker projections or "lightest spot" of the projection.

The computer 17 includes a memory 20 that non-transitory stores executable codes which when executed on a computer make the computer perform the method in FIG. 5 or other similar embodiments described above.

Another embodiment is an apparatus for comparing an intended treatment plan using a radiation source with a delivered plan as illustrated in FIG. 1. The apparatus includes a two dimensional radiation detector (e.g., 15 in FIG. 1) configured to acquire images generated by radiation emitted by the radiation source and a planned 3D position of the radiation source according to the intended treatment plan. The apparatus further includes a plurality of markers (e.g., 16) arranged at known three-dimensional (3D) marker positions between the detector and a planned 3D position of the radiation source according to the intended treatment plan. The apparatus also includes a data processing unit configured (1) to determine projections of the markers on an image detected when the radiation source is located at a treatment position; (2) to calculate a plurality of lines, each line being defined by a 3D position of a marker and a 3D position of a corresponding projection of the marker on the detector according to the image; (3) to infer a 3D position of the radiation source based on the calculated lines; and (4) to compare the inferred 3D position with the planned 3D position.

Figure 6:
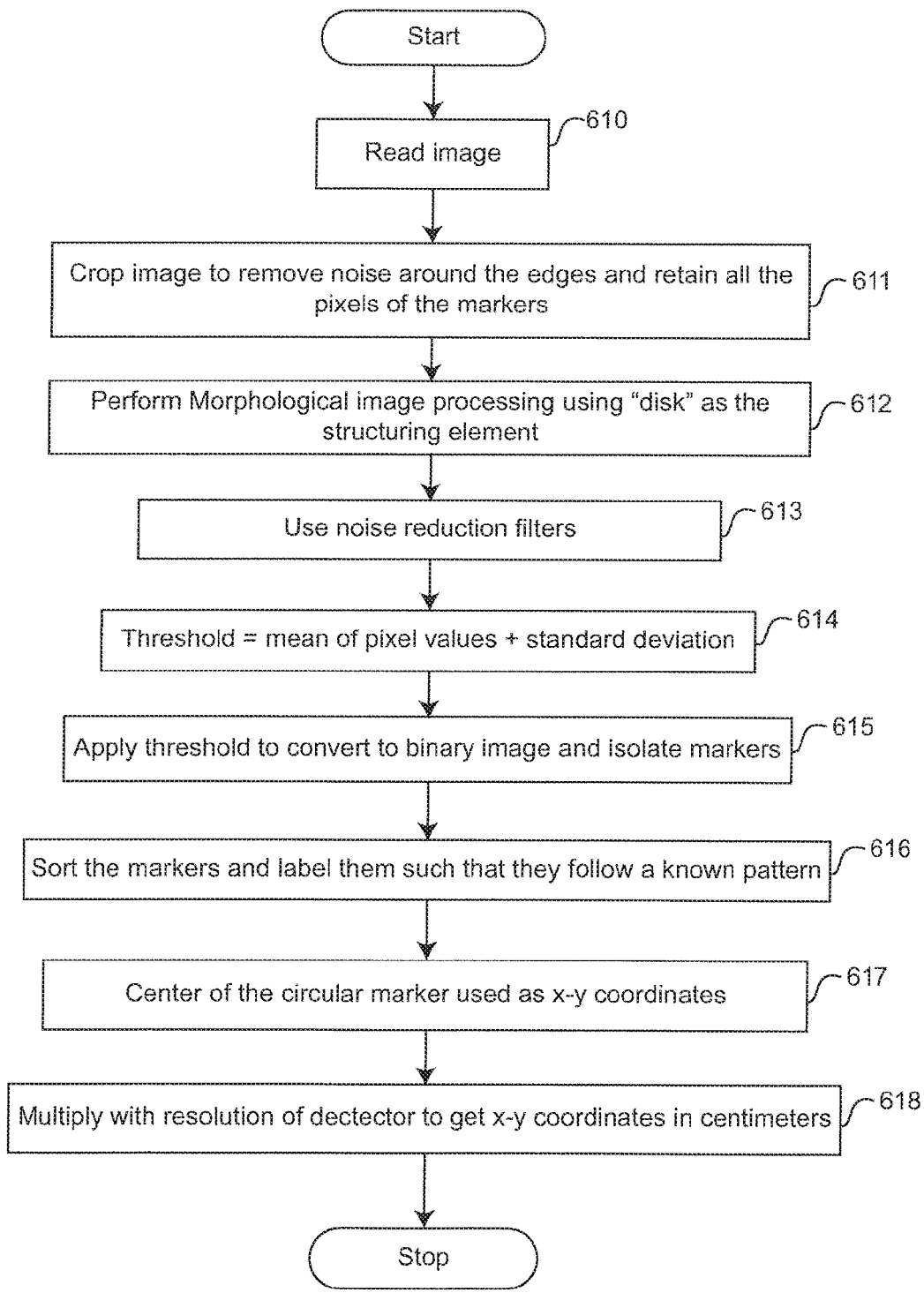
FIG. 6 is a flow diagram illustrating the logic of the image processing algorithm implemented according to the invention.

The specific algorithms implemented according to the invention will now be described. Referring first to FIG. 6, there is shown a flow diagram of the image processing algorithm. The first step at function block 610 is to read the image; that is, the image acquired by the FPD 15 is read by the computer 17 in FIG. 1. Next, in function block 611, the image is cropped to remove noise around the edges and retain all pixels of the markers. In function block 612, morphological image processing is performed using a "disk" as a structuring element. Then, in function block 613, noise reduction filters are used to further reduce the noise in the image. A threshold is established in function block 614 as the mean of pixel values plus the standard deviation. The threshold established in function block 614 is applied in function block 615 to convert the image to a binary image and isolate the markers. Using this binary image, the markers are sorted and labeled in function block 616 such that the markers follow a known pattern. Then in function block 617, the center of the circular marker is used as x-y coordinates. Finally, in function block 618, a multiplication process is performed with the resolution of the FPD 15 to get the x-y coordinates in centimeters (cm).

Figure 7:
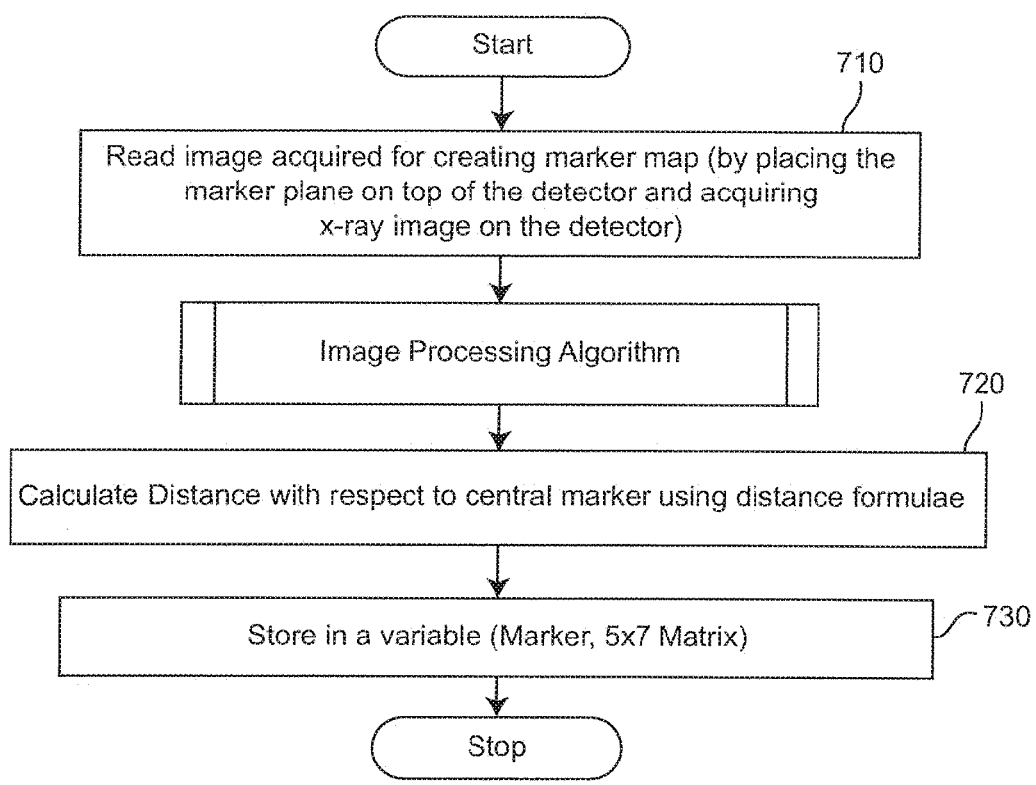
FIG. 7 is a flow diagram illustrating the logic of the marker map process implemented according to the invention.

FIG. 7 is the flow diagram illustrating the logic of the marker map process implemented according to the invention. The first step in this process at function block 710 is to read the image acquired for creating the marker map. This is done by placing the marker plane on top of the detector and acquiring an x-ray image on the FPD. After image processing shown in FIG. 6, a return is made to function block 720, where the distance is calculated with respect to a central marker using distance formulae. The process ends at function block 730 by storing the calculated distances in a variable.

Figure 8:
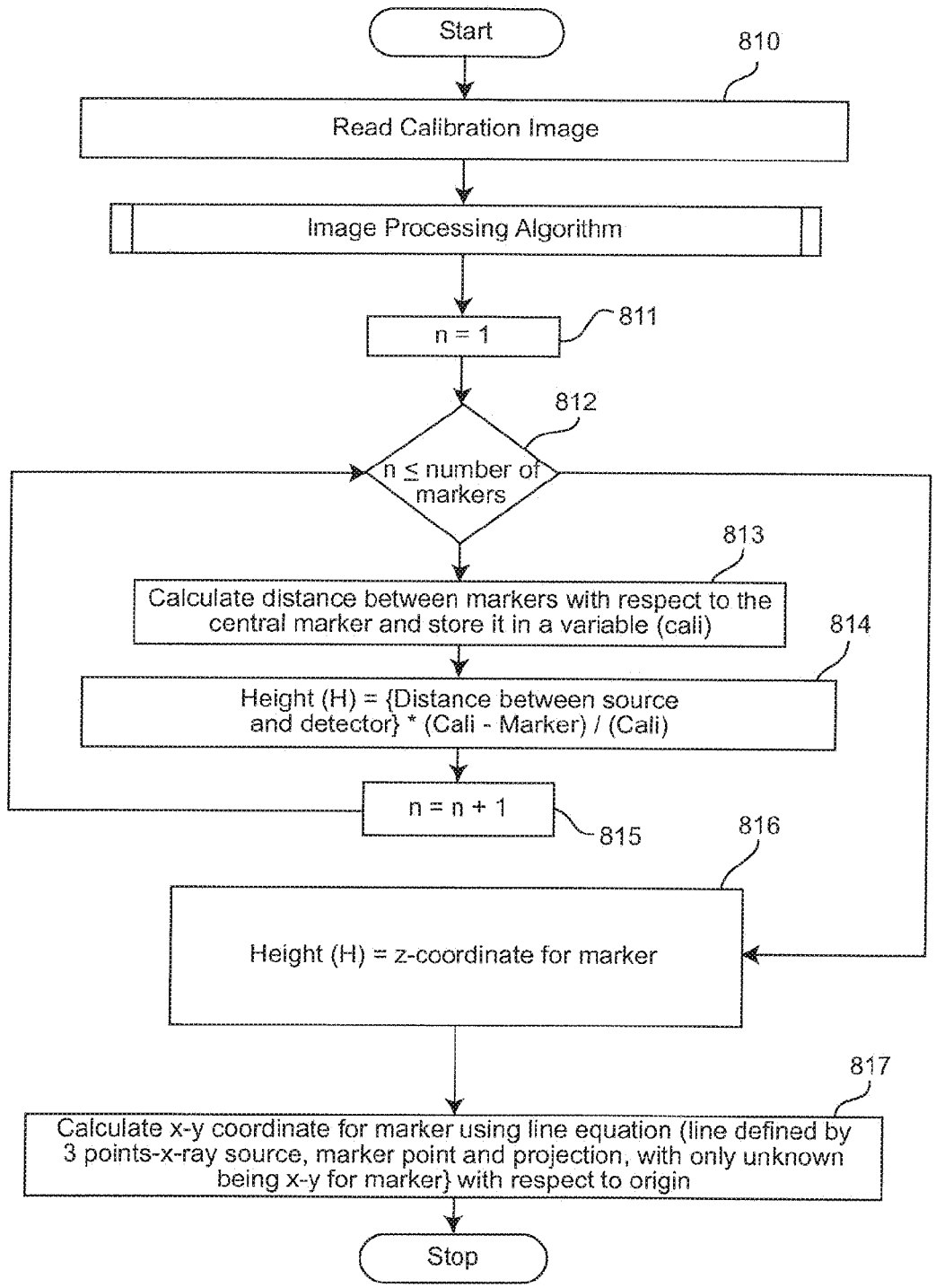
FIG. 8 is a flow diagram illustrating the logic of the calibration algorithm implemented according to the invention.

The calibration algorithm is illustrated in the flow diagram of FIG. 8. The calibration of the panel simply means establishing, prior to patient use, the reconstruction geometry. This is essentially composed of (1) the relative position of the markers in the matrix and (2) the relative position of the panel containing the markers of the panel detector. The first step in function block 810 is read the calibration image. After image processing shown in FIG. 6, a return is made to function block 811, where for purposes of the following iteration, the count "n" is set to 1. Then, in decision block 812, a determination is made as to whether n is less than or equal to the number of markers. Initially, the decision is resolved in the affirmative so that the process next goes to function block 813 where the distance between markers is calculated with respect to the central marker and stored in the a variable "cali". Next, in function block 814, the height H is calculated as the distance between the source and the detector times the difference of the variable cali and the marker divided by the variable cali.

Figure 9:
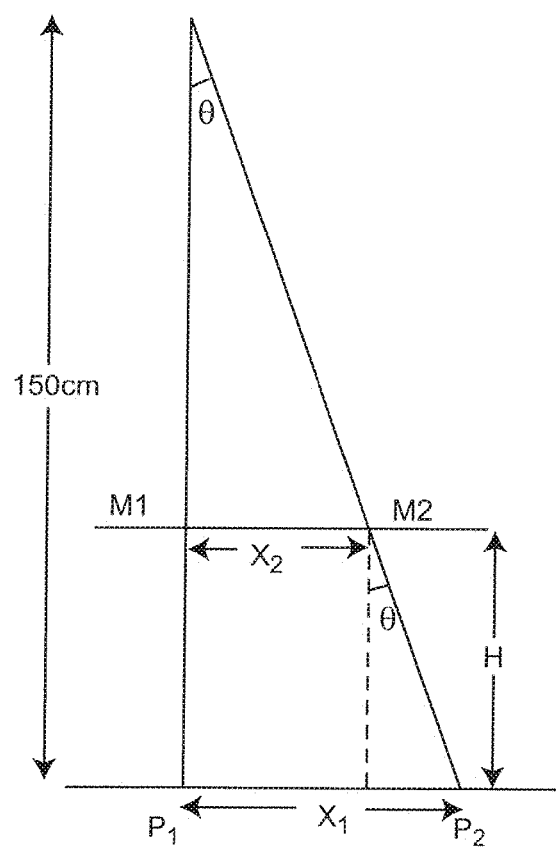
FIG. 9 is a diagram which explains the calculation of H in the process implemented by the calibration algorithm of FIG. 8.

FIG. 9 is a diagram that explains the calculation of H. In FIG. 9, $M_1$ is the central marker and $M_2$ is one of the markers along the central axis; $P_1$ and $P_2$ their respective projections; $X_1$ distance between projections (calculated by software using the calibration image) and $X_2$ distance between markers on the panel (calculated manually from the panel); and H was calculated using the formula below:

$$H = \text{(Distance between source and detector)} * (X_1 - X_2)/X_1$$

Returning to FIG. 8, after the calculation of H for each marker, the count "n" is advanced by 1 in function block 815 before the process returns to decision block 812. At such time as the count "n" exceeds the number of markers, indicating that H has been calculated for all the markers, the process next goes to function block 816 where the calculated value H is established as the z-coordinate for each of the markers. Finally, in function block 817. The x-y coordinate is calculated for each marker using a line equation with respect to the origin.

Figure 10:
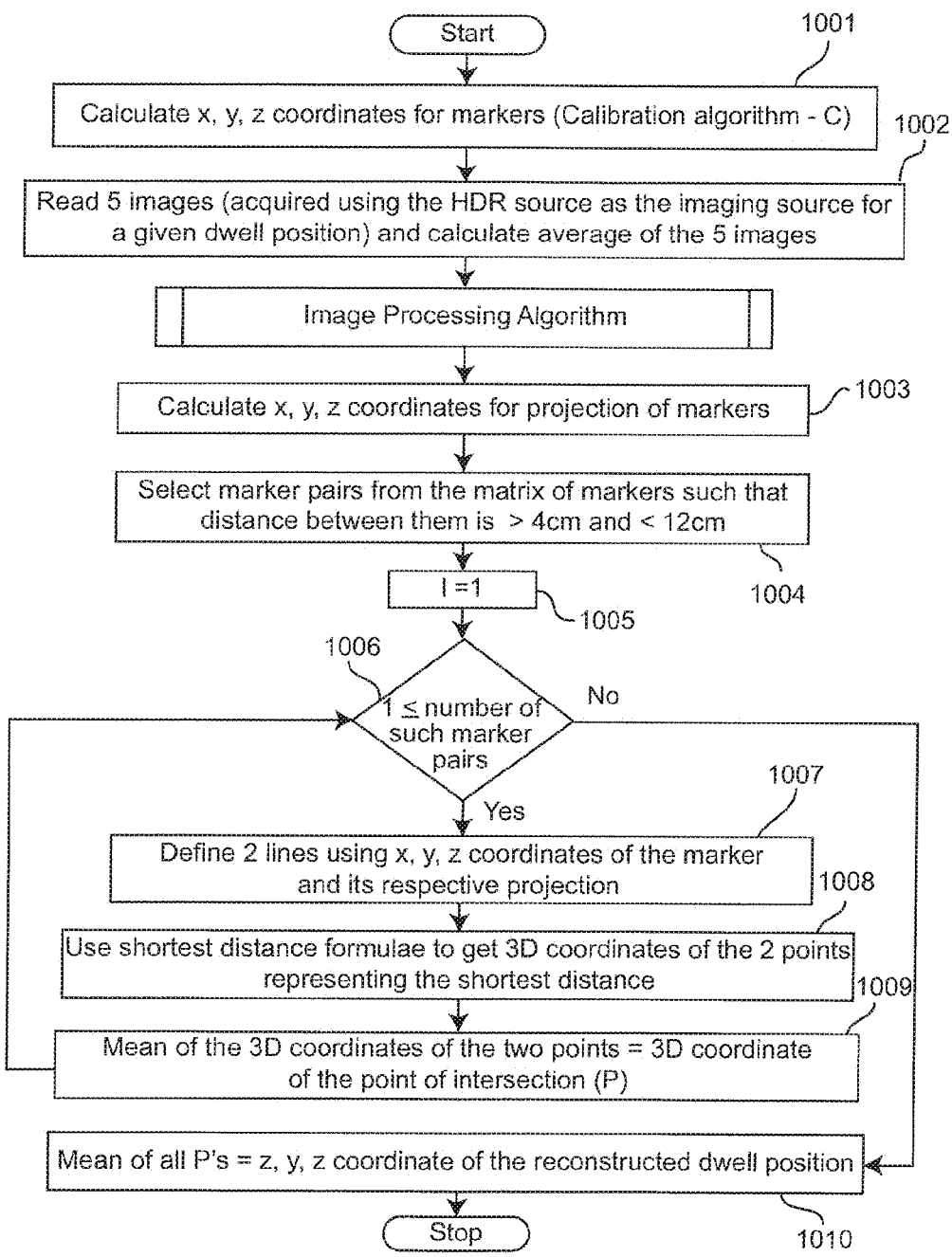
FIG. 10 is a flow diagram illustrating the logic of the reconstruction model process implemented according to the invention.

FIG. 10 is the flow diagram illustrating the logic of the reconstruction algorithm implemented by the invention. In the first step at function block 1001, the x,y,z coordinates for the markers are calculated based on the calibration algorithm of FIG. 8. Then in function block 1002, five images are read. These five images are acquired using the HDR source as the imaging source for a given dwell position. Then the average of the five images is calculated. After image processing shown in FIG. 6, a return is made to function block 1003 where the x,y,z coordinates are calculated for the projection markers. In function block 1004, marker pairs are selected from the matrix such that the distance between them is greater than 4 cm but less than 12 cm. At the beginning of the iteration loop, a count "i" is set to 1 in function block 1005. Then, in decision block 1006, a determination is made as to whether the count "i" is less or equal to the number of such marker pairs. Initially, this will be answered in the affirmative, so the process goes to function block 1007 where two lines are defined using the x,y,z coordinates of the markers and the irrespective projections. Next, in function block 1008, the shortest distance formula is used to get the 3D coordinates of the two points representing the shortest distance. The mean of the 3D coordinates of the two points is set equal to the 3D coordinate of the point of intersection (P) in function block 1009. The count "i" is incremented by one before the process returns to decision block 1006. Once all the marker pairs have been processed, the process goes to function block 1010 where the man of all Ps=x,y,z coordinates of the reconstructed dwell position is calculated.

Figure 11:
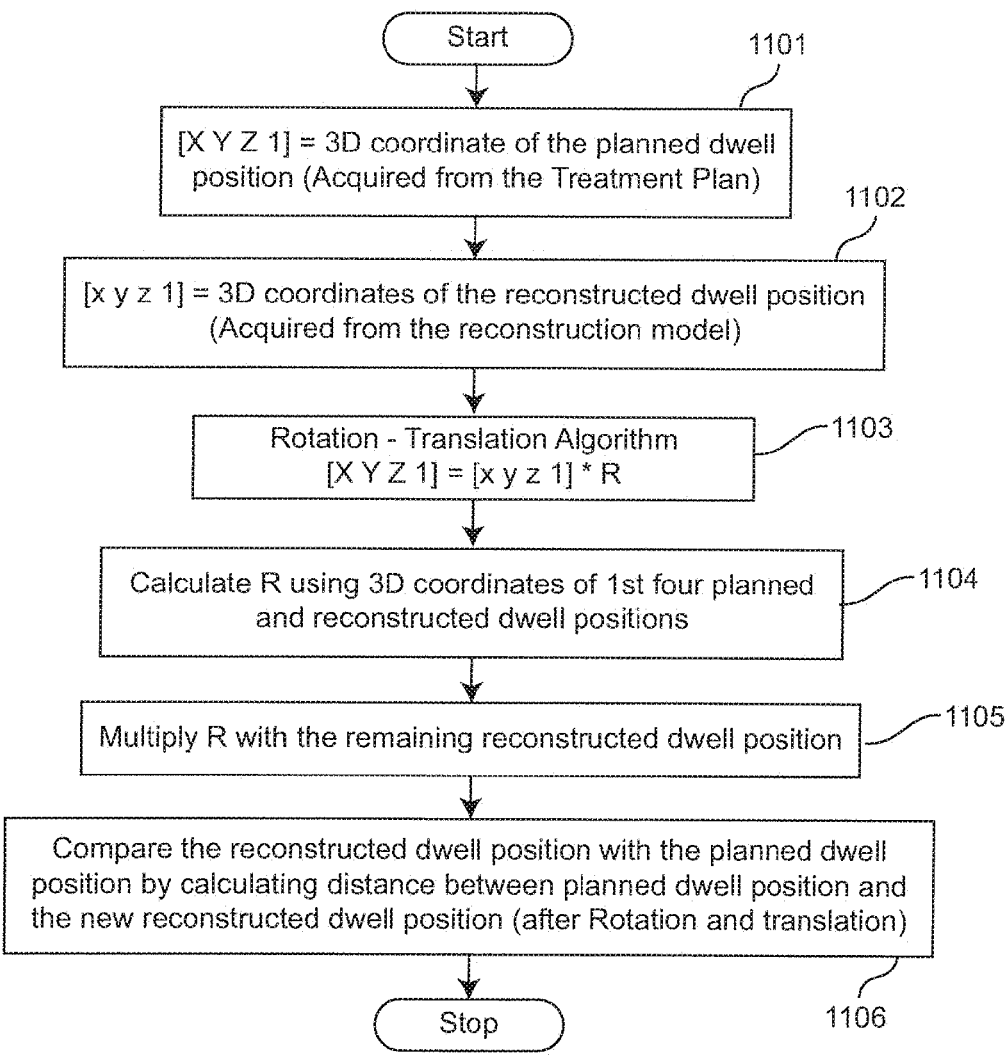
FIG. 11 is a flow diagram illustrating the logic of the rotation translation algorithm implemented according to the invention.

The rotation translation algorithm implemented by the invention is illustrated in the flow diagram of FIG. 11. The process begins at function block 1101 where the [XYZ1=3D coordinates of the planned dwell position as acquired from the treatment plan is read. Then, in function block 1102, the [xyz1]=3D coordinates of the reconstructed dwell position as acquired from the reconstruction model is read. Using a rotation/translation algorithm in function block 1103, [XYZ1] is translated to be equal to [xyz1] times a rotation value R. R is calculated in function block 1104 using the coordinates of the first four planned and reconstructed dwell positions. Then in function block 1105, R is multiplied with the remaining reconstructed dwell positions. Finally, the reconstructed dwell positions are compared in function block 1106 with the planned dwell positions by calculating the distance between planned dwell positions and the new reconstructed dwell positions after rotation and translation.

The foregoing algorithms were implemented in Matlab code; however, those skilled in the art will recognize that other and different programming languages can be used to write code that implements the necessary algorithms.

The disclosed exemplary embodiments provide methods and apparatuses for reconstructing the position of a radiation source during treatment using a two-dimensional flat detector. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or system(s), and performing any incorporated methods. While the invention has been described in terms of its preferred embodiments, those skilled in the are will recognize that the invention can be practiced with modification within the spirit and scope of the appended claims. Accordingly, the present invention should not be limited to the embodiments as described above, but should further include all modifications and equivalents thereof within the spirit and scope of the description provided herein.

What is claimed is:

1. A method for treating a patient with a brachytherapy treatment according to an intended treatment plan, using a radiation source suitable for brachytherapy, comprising the steps of:
    arranging markers at known three-dimensional (3D) positions in a detection reference system between a two dimensional radiation detector configured to acquire images generated by radiation emitted by said radiation source and an area where said radiation source is positioned inside a patient during said brachytherapy treatment;
    determining positions of projections of at least one marker on an image when said radiation source is at a treatment position in an intended treatment plan reference system;
    calculating a plurality of calculated lines in the detection reference system, each line being defined by a 3D position of a marker and a 3D position of a corresponding projection of the marker on the detector according to the image;
    inferring during said brachytherapy treatment a 3D position of said radiation source in the detection reference system based on selected pairs of lines among said plurality of calculated lines, using midpoints of shortest segment between lines in said selected pairs; and
    if no correspondence between the detection reference system and the intended treatment plan reference system is available, matching inferred 3D position with the treatment position to extract the correspondence between the detection reference system and the intended treatment plan reference system; and
    if the correspondence between the detection reference system and the intended treatment plan reference system is available, comparing the inferred 3D position with the treatment position.

2. The method of claim 1, wherein the steps of determining, calculating, inferring and comparing are repeated for a predetermined number of points in the treatment plan, or until a predetermined precision of matching the inferred 3D position with the treatment position is achieved, before making the correspondence between the detection reference system and the intended treatment plan reference system available for performing the step of comparing.

3. The method of claim 1, wherein known 3D positions of the markers are substantially in a plane.

4. The method of claim 3, wherein the plane is substantially parallel to a detector which detects an image of projections of the markers.

5. The method of claim 4, wherein the markers are arranged in a grid having substantially equal distances there between.

6. The method of claim 1, wherein the markers are substantially spherical.

7. The method of claim 1, wherein the markers are made of a radiation absorbing material.

8. The method of claim 1, wherein the step of comparing includes comparing one or more differences between corresponding coordinates of inferred 3D position and coordinates of a planned 3D position with one or more acceptable position deviations.

9. The method of claim 8, wherein the one or more acceptable position deviations have predetermined values.

10. The method of claim 8, further comprising the step of estimating one or more uncertainties of one or more coordinates of inferred 3D position, the one or more acceptable position deviations being defined relative to the one or more uncertainties.

11. The method of claim 8, further comprising the step of generating an alarm when the one or more differences exceed the one or more acceptable position deviations.

12. The method of claim 1, further comprising the step of performing a calibration procedure using substantially perpendicular wires arranged on a plane and placed between said radiation source and the detector.

13. The method of claim 1, wherein the step of inferring includes selecting a subset of lines based on one or more predetermined quality rules.

14. The method of claim 1, wherein the step of calculating includes at least one of:
    identifying marker projections on the image;
    estimating 3D positions of the marker projections based on position estimation rules; and
    selecting a subset of projections among the marker projections on the image based on projection quality rules.

15. A computer readable non-transitory medium storing executable codes which when executed on a computer make the computer perform a method for comparing an intended brachytherapy treatment plan using a radiation source suitable for brachytherapy with a delivered brachytherapy treatment, the method comprising the steps of:
    receiving three-dimensional (3D) marker positions of markers positions in a detection reference system, the markers being located between a two dimensional radiation detector configured to acquire images generated by radiation emitted by said radiation source and an area where said radiation source is positioned during a brachytherapy treatment;
    determining projections of the markers on an image detected when said radiation source is at a treatment position in an intended brachytherapy treatment plan reference system;
    calculating a plurality of lines in said detection reference system, each line being defined by a 3D position of a marker and a 3D position of a corresponding projection of the marker on the detector according to the image;
    inferring a 3D position of said radiation source in the detection reference system based on selected pairs of lines among said plurality of calculated lines, using midpoints of shortest segment between lines in said selected pairs; and
    if no correspondence between said detection reference system and said intended brachytherapy treatment plan reference system is available, matching an inferred 3D position with said treatment position to extract the correspondence between said detection reference system and said intended brachytherapy treatment plan reference system, and
    if the correspondence between said detection reference system and said intended brachytherapy treatment plan reference system is available, comparing said inferred 3D position with said treatment position.

16. An apparatus to compare an intended brachytherapy treatment plan using a radiation source suitable for brachytherapy with a delivered brachytherapy treatment, the apparatus comprising:
    a two dimensional radiation detector configured to acquire images generated by radiation emitted by said radiation source and a planned three-dimensional (3D) position of said radiation source according to said intended brachytherapy treatment plan;
    a plurality of markers arranged at known 3D marker positions between the two dimensional radiation detector and a planned 3D position of said radiation source according to said intended brachytherapy treatment plan; and
    a data processing unit configured
        to determine projections of the markers on an image detected when said radiation source is located at a treatment position,
        to calculate a plurality of lines, each line being defined by a 3D position of a marker and a 3D position of a corresponding projection of the marker on the two dimensional radiation detector according to the image,
        to infer a 3D position of said radiation source based on selected pairs of lines among said plurality of calculated lines, using midpoints of shortest segment between lines in said selected pairs, and
    to compare inferred 3D position with a planned 3D position.

17. A method for real-time three dimensional (3D) high dose rate source position detection and tracking, directing and comparing, in real-time, an intended brachytherapy treatment plan with delivery of a brachytherapy treatment, comprising the steps of:
    developing said intended brachytherapy treatment plan by scanning a patient in a first 3D coordinate system;
    placing a flat panel detector having a matrix of markers at known locations on said flat panel detector at variable heights over the patient;
    detecting projections of markers as images on said flat panel detector produced by said high dose rate source at multiple dwell positions;
    processing the images to obtain a calculated relative position of said high dose rate source in a second 3D coordinate system at each of the multiple dwell positions;
    calculating a transformation of coordinates from the second 3D coordinate system to the first 3D coordinate system; and
    directing said high dose rate source according to said intended brachytherapy treatment plan; and
    comparing a detected position of said high dose rate source at each of the multiple dwell positions with an intended dwell position according to said intended brachytherapy treatment plan,
    whereby the steps of processing, calculating and comparing are performed in real-time to provide a direct correlation of said delivery of brachytherapy treatment with said intended brachytherapy treatment plan.

* * * * *